United States Patent

Bouchard et al.

(10) Patent No.: US 6,818,637 B2
(45) Date of Patent: Nov. 16, 2004

(54) POLYHYDROXYPYRAZINE DERIVATIVES, THEIR PREPARATION AND THE PHARMACEUTICAL COMPOSITIONS WHICH COMPRISE THEM

(75) Inventors: Herve Bouchard, Thiais (FR); Alain Commercon, Vitry-sur-Seine (FR)

(73) Assignee: Aventis Pharma SA, Antony (FR)

( * ) Notice: Subject to any disclaimer, the term of this patent is extended or adjusted under 35 U.S.C. 154(b) by 0 days.

(21) Appl. No.: 09/903,092

(22) Filed: Jul. 11, 2001

(65) Prior Publication Data

US 2002/0077324 A1 Jun. 20, 2002

Related U.S. Application Data

(63) Continuation of application No. PCT/FR00/00026, filed on Jan. 7, 2000.

(30) Foreign Application Priority Data

Jan. 11, 1999 (FR) .............................. 99 00186

(51) Int. Cl.[7] ...................... A61K 31/33; C07D 241/00
(52) U.S. Cl. .................. 514/183; 514/252.12; 544/366; 544/387
(58) Field of Search ............................ 514/184, 252.12; 544/336, 387

(56) References Cited

FOREIGN PATENT DOCUMENTS

| WO | 9718813 | * | 8/1997 |
| WO | 9728813 | * | 8/1997 |

OTHER PUBLICATIONS

Tsuchida et al, Chemical Abstract DN 1056:170812 also cited in as Dev.in Food Sc. 13,85–94(1998).*
PubMed Abstract 12853809, also cited as J. Urol., 170/2, 503–6(2003).*
PubMed Abstract 12853766, also cited as J. Urol. 170/2, 6–14(2003).*
PubMed Abstract 9406614, also cited as Acta Biol. Hung., 48/3/359–67(1997).*
Chemical Abstract DN 1056:170812 also cited as Dev. in Food Sc. 13,85–94(1986).*

* cited by examiner

*Primary Examiner*—Richard L. Raymond
*Assistant Examiner*—Sudhaker B. Patel
(74) *Attorney, Agent, or Firm*—Raymond S. Parker, III

(57) ABSTRACT

The invention concerns novel derivatives of

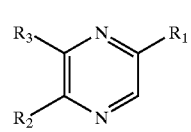

formula (I) wherein: $R_1$ represents the stereoisomeric forms of the chain —$(CHOH)_3$—$CH_2$—O—COR (II) and either $R_2$ represents a hydrogen atom and $R_3$ represents the stereoisomeric forms of the chain —$CH_2$—$(CHOH)_2$—$CH_2$—O—COR (III) or $R_2$ represents the stereoisomeric forms of the chains —$(CHOH)_3$—$CH_2$—O—COR (II) or —$CH_2$—$(CHOH)_2$—$CH_2$—O—COR (III) and $R_3$ represents a hydrogen atom and R represents —$(Alk)_i$—(Cycloalk) radical; i is equal to 0 or 1; Alk represents and alkyl radical, Cycloalk represents a cycloalkyl radical, and their salts with a inorganic or organic acid, their preparation and the medicines containing as active principle at least a product of general formula (I) or its salts with a inorganic or organic acid.

14 Claims, No Drawings

POLYHYDROXYPYRAZINE DERIVATIVES, THEIR PREPARATION AND THE PHARMACEUTICAL COMPOSITIONS WHICH COMPRISE THEM

CROSS REFERENCE TO RELATED APPLICATION

The present application claims benefit under 35 U.S.C. §365(c) to PCT Application serial number FR00/00026, filed Jan. 7, 2000, which is incorporated herein by reference.

The present invention relates to novel products of general formula (I),

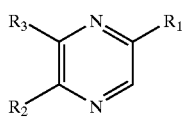
(I)

and to their salts with an inorganic or organic acid, to their preparation, to the pharmaceutical compositions which comprise them and to their use as an antidiabetic agent.

Products exhibiting hypoglycemic properties, of general formula:

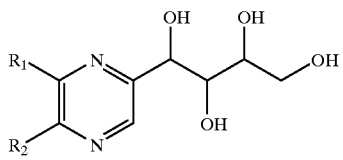

in which either $R_1$ represents a hydrogen atom and $R_2$ represents a chain of formula:

$$CH_2-CHOH-CHOH-CH_2OH \quad (A)$$

$$CHOH-CHOH-CHOH-CH_2OH \quad (B)$$

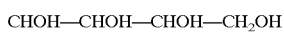

or $R_1$ represents a chain of formula (A) and $R_2$ represents a hydrogen atom, have been disclosed in Application WO 97/28813.

However, nothing in the prior art allowed it to be anticipated that, because of their structural modifications with respect to these products, the products of general formula (I) according to the invention would exhibit greatly improved properties, both in terms of antiglycemic activity and in terms of bioavailability and/or toxicity.

The present invention relates to the products of general formula (I),

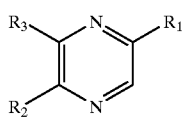
(I)

in which:

$R_1$ represents the stereoisomeric forms of the chain $$-(CHOH)_3-CH_2-O-COR \quad (II)$$

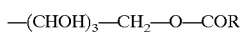

and
either $R_2$ represents a hydrogen atom and $R_3$ represents the stereoisomeric forms of the chain $$CH_2-(CHOH)_2-CH_2-O-COR \quad (III)$$

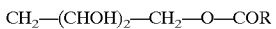

or $R_2$ represents the stereoisomeric forms of the chains $$-(CHOH)_3-CH_2-O-COR \quad (II)$$

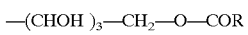

or $$CH_2-(CHOH)_2-CH_2-O-COR \quad (III)$$

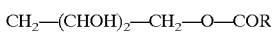

and $R_3$ represents a hydrogen atom
and

R represents an —(Alk)$_i$—(Cycloalk) radical,
for which:
Alk denotes an alkyl radical,
Cycloalk denotes a cycloalkyl radical,
i is equal to 0 or 1;
and
to their stereoisomeric forms and to their salts with an inorganic or organic acid.

The term "alkyl" is understood to mean: a saturated straight- or branched-chain hydrocarbonaceous radical comprising 1 to 6 carbon atoms, such as methyl, ethyl, propyl, isopropyl, butyl, sec-butyl, tert-butyl, pentyl or hexyl.

The term "cycloalkyl" is understood to mean: a saturated cyclic hydrocarbonaceous radical comprising 5 or 6 carbon atoms, such as cyclopentyl or cyclohexyl. The present invention thus relates to the products of general formulae

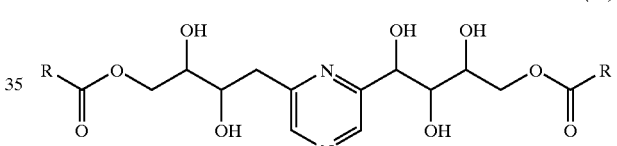
(IV)

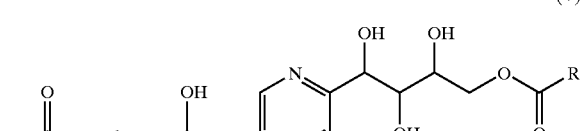
(V)

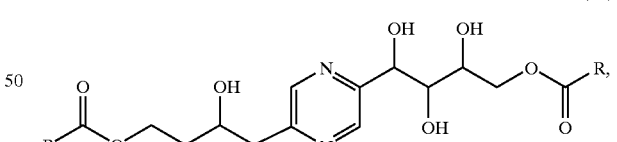
(VI)

in which

R represents an —(Alk)$_i$—(Cycloalk) radical,
for which:
Alk denotes an alkyl radical,
Cycloalk denotes a cycloalkyl radical,
i is equal to 0 or 1;
and to their stereoisomeric forms or to the salts of such products with an organic or inorganic acid. According to the present invention, preference is given to the products having the following general formulae:

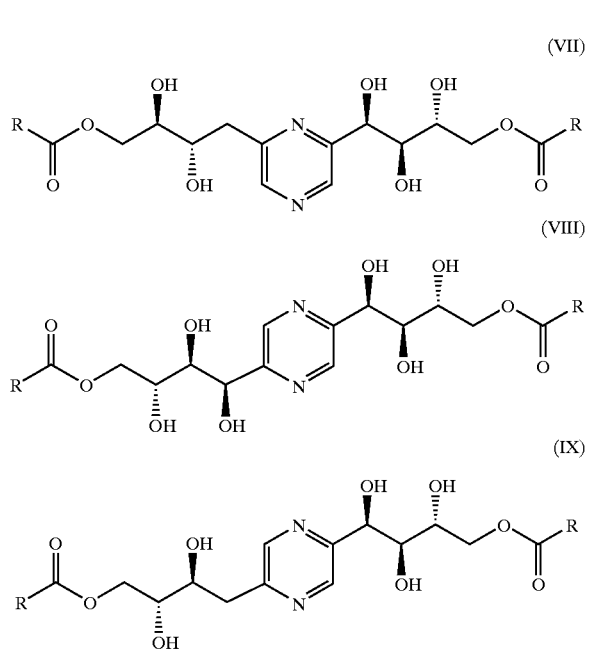

in which

R represents an —(Alk)$_i$—(Cycloalk) radical,
for which:
Alk denotes an alkyl radical,
Cycloalk denotes a cycloalkyl radical,
i is equal to 0 or 1;
and to the salts of such products with an organic or inorganic acid.

More preferably still, the present invention relates to the products of general formula (IX)

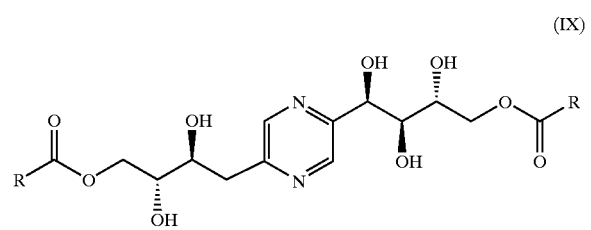

in which:

R represents an —(Alk)$_i$—(Cycloalk) radical,
for which:
Alk denotes an alkyl radical,
Cycloalk denotes a cycloalkyl radical,
i is equal to 0 or 1;
and to the salts of such products with an organic or inorganic acid.

According to an even more advantageous aspect, the present invention relates to the products of general formula (IX) in which:

R represents an —(Alk)$_i$—(Cycloalk) radical,
for which:
Alk denotes the methyl radical,
Cycloalk denotes a cyclohexyl radical,
i is equal to 0 or 1;
and to their salts with an organic or inorganic acid.

The products according to the present invention can very advantageously be chosen individually from:

4,4'-O,O-dicyclohexyloyl-2-[(1R,2S,3R)(1,2,3,4-tetrahydroxylbutyl)]-5-[(2'S,3'R)(2',3',4'-trihydroxy-butyl)]pyrazine 4,4'-O,O-di(cyclohexylacetyl)-2-[(1R,2S,3R)-(1,2,3,4-tetrahydroxylbutyl)]-5-[(2'S,3'R)-(2',3',4'-trihydroxybutyl)]pyrazine and their salts with an inorganic or organic acid.

In particular: 4,4'-O,O-dicyclohexyloyl-2-[(1R,2S,3R)(1,2,3,4-tetrahydroxylbutyl)]-5-[(2'S,3'R)(2',3',4'-trihydroxybutyl)]pyrazine and its salts with an inorganic or organic acid.

According to the present invention, the products of general formula (I) in which R is defined as above can be obtained from the products of general formula:

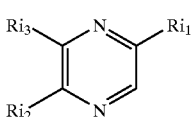 (X)

in which:

Ri$_1$ represents the stereoisomeric forms of the chain

—(CHOH)$_3$—CH$_2$OH  (XI)

and

Ri$_2$ represents a hydrogen atom and Ri$_3$ represents the stereoisomeric forms of the chain

—CH$_2$—(CHOH)$_2$—CH$_2$OH  (XII)

or Ri$_2$ represents the stereoisomeric forms of the chains

—(CHOH)$_3$—CH$_2$OH  (XI)

or

—CH$_2$—(CHOH)$_2$—CH$_2$OH  (XII)

and Ri$_3$ represents a hydrogen atom,
by reaction with a corresponding acyl halide of formula R—COX, in which R is defined as above and X represents a halogen atom, such as chlorine.

This reaction is carried out in the presence of an organic or inorganic base, preferably pyridine, at temperatures of between 0 and 40° C.

The acyl halide of formula R—COX, in which R is defined as above and X represents a halogen atom, such as chlorine, may be commercially available or optionally can be prepared from the corresponding acid R—COOH according to the usual methods; in particular, the acyl chloride can be prepared from the corresponding acid by reaction with oxalyl chloride in a solvent, such as dichloromethane, N,N-dimethylformamide or a mixture of these two solvents.

The acyl halide can advantageously be prepared in situ. The products of general formula (X) can be prepared in the following way:

The stereoisomeric forms of the products of general formula (X) are obtained from the stereoisomeric forms of the reactants hereinbelow used by the preparation process according to the invention.

The stereoisomers of the products of formula (X) in which Ri$_1$ represents the stereoisomeric forms of the —(CHOH)$_3$—CH$_2$OH chain (XI), Ri$_2$ represents a hydrogen atom and Ri$_3$ represents the stereoisomeric forms of the —CH$_2$—(CHOH)$_2$—CH$_2$OH chain (XII) can be obtained by reaction of ammonium formate with an aldose, or a mixture of 2 aldoses, of the dextrorotatory or levorotatory series, of general formula:

$$CHO-CHOH-Ri_1 \qquad (XIII)$$

in which $Ri_1$ has the same meaning as in the formula (X)

This reaction can preferably be carried out at a temperature of between 15° C. and 100° C., preferably in aqueous medium.

The aldoses are commercially available or can be obtained from:

a) commercially available aldoses: by epimerization reactions, by application or adaptation of the methods described in Adv. Carbohydr. Chem., 13, 63, (1958), in particular in basic medium by means of a dilute aqueous sodium hydroxide solution (0.03 to 0.05%), at a temperature of between 20 and 40° C.,
by chain-extension reactions, by application or adaptation of the methods described in "The Carbohydrates", edited by W. Pigman and D. Horton, Academic Press, New York, Volume IA, 133 (1972), and in particular by forming the cyanohydrin of the starting aldose (for example, by reaction with sodium cyanide in aqueous solution, at a temperature of between 10 and 30° C. and in the presence of sodium hydroxide, at a pH in the region of 9), then hydrolysis of the nitrile functional group thus formed to the corresponding acid by application or adaptation of the methods described in Organic Synthesis, Volume I, page 436 and Volume III, page 85 (for example, using concentrated sulfuric acid or hydrochloric acid, in aqueous solution, at a temperature of between 20° C. and the reflux temperature of the reaction mixture), and then reduction of the carboxylic acid functional group to the corresponding aldehyde by application or adaptation of the methods described in J. Am. Chem. Soc., 71, 122 (1949), in particular using an alkali metal borohydride (for example, sodium borohydride), in aqueous solution, at a temperature of between 20° C. and the boiling temperature of the reaction mixture, by chain-shortening reactions, by application or adaptation of the methods described in "The Carbohydrates", edited by W. Pigman and D. Horton, Academic Press, New York, Volume IB, 1980, page 929 or Chem. Ber., 83, 559 (1950) and in particular by converting the aldehyde functional group of the aldose to the corresponding hydroxylamine by application or adaptation of the methods described in Organic Synthesis, Volume II, page 314 (for example, using hydroxylamine hydrochloride, in aqueous solution and in the presence of a base, such as sodium carbonate, at a temperature of between 20 and 50° C.), and then reaction with 3,4-dinitrofluorobenzene in the presence of carbon dioxide and a base, such as sodium hydrogencarbonate, in aqueous solution, and an aliphatic alcohol (for example, isopropyl alcohol), at a temperature of between 50 and 80° C., b) corresponding allyl alcohols, by application or adaptation of the methods described in Science, 220, 949 (1983) and in particular using tert-butyl hydroperoxide in the presence of a titanium(IV) complex, such as the titanium(IV) isopropoxide and optically pure dialkyl tartrate (for example, diethyl tartrate) complex, followed by successive reaction with sodium thiophenolate, para-chloroperbenzoic acid in acetic anhydride, and diisopropylaluminum hydride.

The stereoisomers of the sugar of formula (XIII) can be those of aldoses comprising 6 carbon atoms; those prefer-ably used are D-glucose, D-gulose, D-mannose, D-galactose, D-allose, D-altrose, D-idose, D-talose, L-glucose, L-mannose, L-galactose, L-allose, L-altrose, L-idose, L-talose or L-gulose.

The stereoisomers of the products of formula (X) in which $Ri_1$ represents the stereoisomeric forms of the $-(CHOH)_3-CH_2OH$ chain (XI), $Ri_2$ represents the stereoisomeric forms of the $-(CHOH)_3-CH_2OH$ chains (XI) and $Ri_3$ represents a hydrogen atom can be obtained by treatment, in basic medium, of an aminoaldose, or of a mixture of 2 aminoaldoses, of general formula:

$$CHO-CH(NH_2)-Ri_1 \qquad (XIV)$$

optionally in the form of an addition salt, such as the hydrochloride, in which $Ri_1$ has the same meaning as in the general formula (X).

The reaction is preferably carried out at a temperature in the region of 20° C. and use is preferably made of an aqueous ammonia solution and more particularly a 28% solution.

The aminoaldoses of formula (XIV) are commercially available or can be prepared by application or adaptation of methods described in, for example:

(a) Methods Carbohydr. Chem., 7, 29 (1976), which consist in converting the aldehyde functional group of the corresponding aldose to a nitroethylene group using nitromethane in basic medium (for example, sodium ethoxide) and in then successively treating the product obtained with a saturated aqueous ammonia solution, at a temperature of between 20° C. and 30° C., with $Ba(OH)_2$ in aqueous solution, at a temperature of between 20° C. and 30° C., and finally [lacuna] dilute sulfuric acid (10 to 15%), at a temperature of between 20° C. and 30° C., (b) "The Amino Sugar", edited by R. W. Jeanloz, Academic Press, New York, 1969, page 1 or "The Carbohydrates", edited by W. Pigman and D. Horton, Academic Press, New York, Volume IB, 1980, page 664, which consist in converting the aldehyde functional group of the corresponding aldose to an imino group from a primary aromatic amine (for example aniline) and of subsequently successively reacting [lacuna] hydrocyanic acid, at a temperature of between 0° C. and 20° C., and [lacuna] hydrogen in the presence of palladium, in a solvent such as an ether (for example, tetrahydrofuran) or an aliphatic alcohol (for example, ethanol or methanol), at a temperature of between 20° C. and 50° C.

The stereoisomers of the aminoaldose of formula (XIV) can be those of aminoaldose comprising 6 carbon atoms, such as D-glucosamine, D-galactosamine, L-glucosamine or L-galactosamine; those preferably used are D-glucosamine or D-galactosamine and in particular D-glucosamine, optionally in the form of an addition salt, such as the hydrochloride.

The stereoisomers of the products of formula (X) in which $Ri_1$ represents the stereoisomeric forms of the $-(CHOH)_3-CH_2OH$ chain (XI), $Ri_2$ represents the stereoisomeric forms of the $-CH_2-(CHOH)_2-CH_2OH$ chains (XII) and $Ri_3$ represents a hydrogen atom can be obtained either from an aminoaldose, or from a mixture of 2 aminoaldoses, of general formula:

$$CHO-CH(NH_2)-Ri_1 \qquad (XIV)$$

in which $Ri_1$ has the same meaning as in the general formula (I), in acidic medium and more particularly in acetic acid medium and preferably while carrying out the reaction at a temperature of between 15° C. and 100° C., or from a ketose, or from a mixture of 2 ketoses, of general formula:

HOCH$_2$CO—Ri$_1$ (XV)

in which Ri$_1$ has the same meaning as in the general formula (X), by reaction with ammonium formate and preferably while carrying out the reaction at a temperature of between 15° C. and 100° C. and preferably in aqueous medium.

The ketoses of formula (XV) are commercially available or can be prepared by application or adaptation of the methods described in, for example:

a) Adv. Carbohydr. Chem., 13, 63, (1958), which consist in reacting the corresponding aldose either with a base, such as calcium hydroxide, sodium hydroxide, pyridine or quinoline, or with an acid, such as sulfuric acid, in aqueous solution or in the pure phase, at a temperature of between 20 and 50° C., b) Tetrahedron Asymmetry, 7(8), 2185, (1996), J. Am. Chem. Soc., 118(33), 7653 (1996), J. Org. Chem., 60(13), 4294 (1995), Tetrahedron Lett., 33(36), 5157 (1992), J. Am. Chem. Soc., 113(17), 6678 (1991), Angew. Chem., 100(5), 737, (1988), J. Org. Chem., 57, 5899 (1992), which consist, for example, in condensing either hydroxypyruvaldehyde, 1,3-dihydroxyacetone, 1,3-dihydroxyacetone monophosphate or hydroxypyruvic acid with a 2-hydroxyacetaldehyde which is substituted in the 2 position and which is optionally optically pure, optionally in the presence of an enzyme, such as a transketolase. This reaction is generally carried out in an aqueous solution, at a temperature of between 20 and 50° C., optionally in the presence of a base (for example, sodium hydroxide), of barium chloride, of magnesium chloride or of zinc chloride. Derivatives possessing a 2-hydroxyacetaldehyde group are commercially available or can be prepared from aldoses by application or adaptation of the methods described in P. Collins and R. Ferrier, Monosaccharides, Their Chemistry and Their Roles in Natural Products, published by J. Wiley (1995), and M. Bols, Carbohydrate Building Blocks, published by J. Wiley (1996).

The aminoaldoses of formula (XIV) can be those of aminoaldose comprising 6 carbon atoms, such as D-glucosamine, D-galactosamine, L-glucosamine or L-galactosamine; those preferably used are D-glucosamine or D-galactosamine and in particular D-glucosamine, optionally in the form of an addition salt, such as the hydrochloride.

The stereoisomers of the products of formula (XV) can be those of ketoses comprising 6 carbon atoms; those preferably used are D-psicose, D-fructose, D-sorbose, D-tagatose, L-psicose, L-fructose, L-sorbose or L-tagatose.

The reaction mixtures obtained by the various processes described above are treated according to conventional physical (evaporation, extraction, distillation, chromatography or crystallization, for example) or chemical (formation of salts, for example) methods.

The products of formula (I) can optionally be converted to addition salts with an inorganic or organic acid by the action of such an acid in a solvent, such as an alcohol, a ketone, an ether or a chlorinated solvent. These salts also form part of the invention.

Mention may be made, as examples of pharmaceutically acceptable salts, of the addition salts with inorganic or organic acids, such as acetate, propionate, succinate, benzoate, fumarate, maleate, oxalate, methanesulfonate, isethionate, theophyllinacetate, salicylate, methylenebis(b-oxynaphthoate), hydrochloride, sulfate, nitrate and phosphate.

The products of formula (I) exhibit advantageous pharmacological properties. They are of hypoglycemic type.

The hypoglycemic activity of the products of formula (I) was determined with respect to the hyperglycemic response to the oral administration of glucose in the normoglycemic mouse, according to the protocol described in Example 3.

The products of general formula (I) according to the invention exhibit a low toxicity. Their LD$_{50}$ is greater than 2000 mg/kg via the oral route in the mouse.

In human therapeutics, these products are useful in the prevention and treatment of diabetes and in particular type II diabetes (NID diabetes), obese diabetes, diabetes at the age of about fifty, metaplethoric diabetes, diabetes affecting the elderly and mild diabetes. They can be used as a supplement to insulin therapy in insulin-dependent diabetes where they make it possible to gradually reduce the dose of insulin, unstable diabetes, insulin-resistant diabetes, and as a supplement to hypoglycemic sulfamides when these do not provide a sufficient decrease in glycemia. These products can also be used in complications of diabetes, such as hyperlipemias, lipid metabolism disorders, dyslipemias and obesity. They are also useful in the prevention and treatment of lesions of atherosclerosis and their complications (coronopathies, myocardial infarction, cardiomyopathies, progression of these three complications into left ventricular insufficiency, various arteriopathies, arterites of the lower limbs with claudication and progression into ulcers and gangrene, cerebral vascular insufficiency and its complications and sexual impotence of vascular origin), diabetic retinopathy and all its manifestations (increase in capillary permeability, capillary thrombosis and dilation, microaneurysms, arteriovenous shunt, venous dilation, punctiform and macular hemorrhages, exudates, macular edemas, manifestations of proliferative retinopathy: neovessels, proliferative retinitis scars, hemorrhages of the vitreous body, retinal detachment), diabetic cataract, diabetic neuropathy in its various forms (peripheral polyneuropathies and its manifestations such as paresthesias, hyperesthesias and pain, mononeuropathies, radiculopathies, autonomous neuropathies, diabetic amyotrophies), manifestations of diabetic foot (ulcers of the lower extremities and of the foot), diabetic nephropathy in its two diffuse and nodular forms, atheromatosis (rise in HDL lipoproteins promoting the elimination of cholesterol from the atheroma plaques, decrease in the LDL lipoproteins, decrease in the LDL/HDL ratio, inhibition of oxidation of the LDLs, decrease in plaque adhesiveness), hyperlipemias and dyslipemias (hypercholesterolemias, hypertriglyceridemias, normalization of the fatty acid level, normalization of uricemia, normalization of the A and B apoproteins), cataracts, arterial hypertension and its consequences.

The medicaments according to the invention are composed of a product according to the invention or a combination of these products, in the pure state or in the form of a composition in which it is combined with any other pharmaceutically compatible product, which can be inert or physiologically active. The medicaments according to the invention can be employed orally, parenterally, rectally or topically.

As solid compositions for oral administration, there can be used tablets, pills, powders (gelatin capsules, cachets) or granules. In these compositions, the active principle according to the invention is mixed with one or more inert diluents, such as starch, cellulose, sucrose, lactose or silica, under an argon stream. These compositions can also comprise substances other than the diluents, for example one or more lubricants such as magnesium stearate or talc, a colorant, a coating (dragees) or a glaze.

As liquid compositions for oral administration, there can be used pharmaceutically acceptable solutions, suspensions, emulsions, syrups and elixirs containing inert diluents, such as water, ethanol, glycerol, vegetable oils or liquid paraffin. These compositions can comprise substances other than the diluents, for example wetting, sweetening, thickening, flavouring or stabilizing products.

The sterile compositions for parenteral administration can preferably be solutions in aqueous or nonaqueous form, suspensions or emulsions. As solvent or vehicle, there can be employed water, propylene glycol, a polyethylene glycol, vegetable oils, in particular olive oil, injectable organic esters, for example ethyl oleate, or other suitable organic solvents. These compositions can also contain adjuvants, in particular wetting, isotonizing, emulsifying, dispersing and stabilizing agents. Sterilization can be performed in several ways, for example by aseptizing filtration, by incorporating sterilizing agents into the composition, by irradiation or by heating. They can also be prepared in the form of sterile solid compositions which can be dissolved at the time of use in sterile water or any other injectable sterile medium.

The compositions for rectal administration are suppositories or rectal capsules which contain, in addition to the active product, excipients such as cocoa butter, semisynthetic glycerides or polyethylene glycols.

The compositions for topical administration can be, for example, creams, lotions, collyria, collutoria, nose drops or aerosols.

The doses depend on the desired effect, the duration of treatment and the administration route used; they are generally between 150 mg and 600 mg per day via the oral route for an adult with unit doses ranging from 50 mg to 200 mg of active substance.

In general, the doctor will determine the appropriate dosage according to the age, weight and all other factors specific to the subject to be treated.

The following Example 4 illustrates compositions according to the invention.

The invention also relates to the use of the products of general formula (I) in the preparation of pharmaceutical compositions of use in the treatment and/or prevention of diabetes and complications of diabetes.

The following examples illustrate more particularly and without implied limitation the preparation process used according to the invention. It is part of the general knowledge of a person skilled in the art to apply or adapt these methods in order to implement the invention.

EXAMPLE 1

4,4'-O,O-Dicyclohexyloyl-2-[(1R,2S,3R)(1,2,3,4-tetrahydroxylbutyl)]-5-[(2'S,3'R)(2',3',4'-trihydroxybutyl)] pyrazine 0.328 cm³ of cyclohexanoyl chloride are added dropwise, at a temperature in the region of 20° C. under an argon atmosphere, to 300 mg of 2-[(1R,2S,3R)(1,2,3,4-tetrahydroxybutyl)]-5-[(2'S,3'R)(2',3',4'-trihydroxybutyl)] pyrazine in suspension in 7.5 cm³ of pyridine dried over 4 Å molecular sieve. The white reaction suspension is stirred for 15 hours at a temperature in the region of 20° C. The reaction medium is diluted with 30 cm³ of ethyl acetate and 30 cm³ of distilled water. After separation by settling, the organic phase is washed with 20 cm³ of a saturated aqueous sodium chloride solution, dried over magnesium sulfate, filtered through a sintered glass funnel and then concentrated to dryness under reduced pressure (0.2 kPa) at a temperature in the region of 40° C. A yellow oil is obtained, which oil is purified by preparative chromatography on 4 60F254 Merck silica gel plates (thickness=0.5 mm, 20×20 cm), elution being carried out with a dichloromethane/methanol (90/10 by volume) mixture. The fractions comprising only the desired products are extracted with a dichloromethane/methanol (80/20 by volume) mixture, filtered through a sintered glass funnel and then concentrated to dryness under reduced pressure (0.5 kPa) at a temperature in the region of 40° C. 23.3 mg of 4,4'-O,O-dicyclohexyloyl-2-[(1R,2S,3R) (1,2,3,4-tetrahydroxylbutyl)]-5-[(2'S,3'R)(2',3',4'-trihydroxybutyl)]pyrazine are thus obtained in the form of a white solid.

The product obtained has the following characteristics:

¹H NMR spectrum (400 MHz, d6-(CD₃)₂SO, δ in ppm): from 1.10 to 1.95 (mt, 20H in total, cyclohexyl CH₂), 2.34 (mt, 2H, OCOCH), 2.76 and 3.12 (2 dd, respectively J=14 and 10 Hz and J=14 and 3 Hz, each 1H, 5α CH₂), from 3.50 to 3.65 (mt, 1H, 5γ CH), 3.60 (broad t, J=8.5 Hz, 1H, 2β CH), 3.78 (mt, 1H, 5β CH), 3.86 (mt, 1H, 2γ CH), from 3.95 to 4.05 (mt, 2H, 1H of the 5δ CH₂O and 1H of the 2δ CH₂O), 4.24 (dd, J=11 and 3 Hz, 1H, the other H of the 5δ CH₂O), 4.30 (dd, J=12 and 2.5 Hz, 1H, the other H of the 2δ CH₂O), 4.63 (d, J=8.5 Hz, 1H, OH at 2β), 4.86 (d, J=7 Hz, 1H, OH at 5β), 4.97 (broad d, J=6.5 Hz, 1H, 2α CH), 5.05 (d, J=6 Hz, 1H, OH at 2γ), 5.11 (d, J=6 Hz, 1H, OH at 5γ), 5.40 (d, J=6.5 Hz, 1H, OH at 2α), 8.43 (broad s, 1H, =CH at 6), 8.67 (broad s, 1H, =CH at 3).

2-[(1R,2S,3R)(1,2,3,4-Tetrahydroxybutyl)]-5-[(2'S,3'R) (2',3',4'-trihydroxybutyl)]pyrazine can be prepared from D-glucosamine in the presence of acetic acid or by application or adaptation of the methods described in Advances in Carbohydrate Chemistry and Biochemistry, Academic Press, New York, Vol. 25, 1970, 311–349.

EXAMPLE 2

4,4'-O,O-Di(cyclohexylacetyl)-2-[(1R,2S,3R)-(1,2,3,4-tetrahydroxylbutyl)]-5-[(2'S,3'R)-(2',3',4'-trihydroxybutyl)] pyrazine

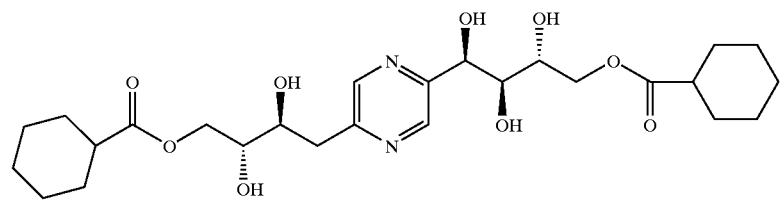

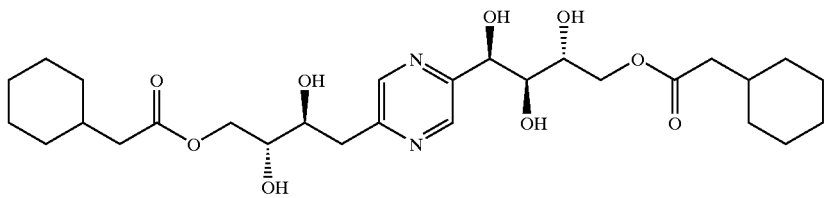

0.26 cm³ of oxalyl chloride are added dropwise, at a temperature in the region of 20° C. under an argon atmosphere, to 350 mg of cyclohexaneacetic acid in 2 cm³ of dichloromethane dried over 4 Å molecular sieve. The reaction mixture is stirred at a temperature in the region of 20° C. for 1 hour, at the end of which time the initial gas evolution has disappeared.

The acid chloride solution prepared above is added dropwise, at a temperature in the region of 20° C. under an argon atmosphere, to 300 mg of 2-[(1R,2S,3R)(1,2,3,4-tetrahydroxybutyl)]-5-[(2'S,3'R)(2',3',4'-trihydroxybutyl)]pyrazine in suspension in 7.5 cm³ of pyridine dried over 4 Å molecular sieve. The white reaction suspension is stirred for 17 hours at a temperature in the region of 20° C. The reaction medium is partially concentrated under an air stream at a temperature in the region of 20° C. and then purified by preparative chromatography on 4 60F254 Merck silica gel plates (thickness=0.5 mm, 20×20 cm), elution being carried out with a dichloromethane/methanol (90/10 by volume) mixture. The fractions comprising only the desired products are extracted with a dichloromethane/methanol (80/20 by volume) mixture, filtered through a sintered glass funnel and then concentrated to dryness under reduced pressure (0.5 kPa) at a temperature in the region of 40° C. 31.5 mg of 4,4'-O,O-di(cyclohexylacetyl)-2-[(1R,2S,3R)(1,2,3,4-tetrahydroxylbutyl)]-5-[(2'S,3'R)(2',3',4'-trihydroxybutyl)]pyrazine are thus obtained in the form of a white solid.

The product obtained has the following characteristics:

$^1$H NMR spectrum (400 MHz, d6-(CD$_3$)$_2$SO, δ in ppm): from 0.85 to 1.80 (mt, 22H in total, cyclohexyl CH and CH$_2$), 2.20 (mt, 4H, OCOCH$_2$), 2.76 and 3.13 (2 dd, respectively J=14 and 10 Hz and J=14 and 3 Hz, each 1H, 5α CH$_2$), from 3.50 to 3.65 (mt, 1H, 5γ CH), 3.60 (broad t, J=8.5 Hz, 1H, 2β CH), 3.78 (mt, 1H, 5β CH), 3.84 (mt, 1H, 2γ CH), from 3.95 to 4.10 (mt, 2H, 1H of the 5δ CH$_2$O and 1H of the 2δ CH$_2$O), 4.25 (dd, J=11 and 3 Hz, 1H, the other H of the 5δ CH$_2$O), 4.30 (dd, J=12 and 2.5 Hz, 1H, the other H [lacuna] 2δ CH$_2$O), 4.62 (d, J=8.5 Hz, 1H, OH at 2β), 4.86 (d, J=7 Hz, 1H, OH at 5β), 4.96 (broad d, J=6.5 Hz, 1H, 2α CH), 5.05 (d, J=6 Hz, 1H, OH at 2γ), 5.11 (d, J=6 Hz, 1H, OH at 5γ), 5.41 (d, J=6.5 Hz, 1H, OH at 2α), 8.43 (d, J=1 Hz, 1H, =CH at 6), 8.67 (broad s, 1H, =CH at 3).

2-[(1R,2S,3R)(1,2,3,4-Tetrahydroxybutyl)]-5-[(2'S,3'R)(2',3',4'-trihydroxybutyl)]pyrazine can be prepared from D-glucosamine in the presence of acetic acid or by application or adaptation of the methods described in Advances in Carbohydrate Chemistry and Biochemistry, Academic Press, New York, Vol. 25, 1970, 311–349.

EXAMPLE 3

Swiss albino mice weighing between 22 and 26 g are left without nourishment for 2 hours. At the end of this period, the glycemia is measured and, immediately after, a dose of glucose (2 g/kg) is administered orally. Thirty minutes later, the glycemia is once again measured. The mice which respond by a hyperglycemia greater than 170 mg/dl are selected and used to detect the hypoglycemic activity of the products according to the invention.

The mice thus chosen are divided into groups of at least 10 animals. Several groups receive doses of 3 to 50 mg/kg of product in a vehicle, such as water or a mixture of methylcellulose/tween and water, once daily by gastric intubation. The treatment lasts 4 days. On the 4$^{th}$ day, after the final treatment, the animals receive a dose of glucose (2 g/kg) and the glycemia is measured 20 to 40 minutes later. The percentage of inhibition of the hyperglycemic response to the administration of glucose is calculated with respect to the response measured in the group treated with the vehicle.

In this test, the products according to the invention exhibit a percentage of inhibition of glycemia of greater than or equal to 10%.

A compartive test according to the protocol described above was carried out with the product of Example 1 according to the present invention and the reference product 2-(1,2,3,4-tetrahydroxybutyl)-5-(2',3',4'-trihydroxybutyl)]pyrazine, the antidiabetic activity of which was disclosed in Application WO 97/28813:

The results obtained after an administration at 3 mg/kg demonstrate the relative activity of the product of Example 1 of 149% with respect to the reference product.

EXAMPLE 4

EXAMPLE 4A

Hard gelatin capsules, with doses of 50 mg of active product, having the following composition are prepared according to the usual technique:

| | |
|---|---|
| Active product | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE 4B

Tablets, with doses of 50 mg of active product, having the following composition are prepared according to the usual technique:

| | |
|---|---|
| Active product | 50 mg |
| Lactose | 104 mg |
| Cellulose | 40 mg |
| Polyvidone | 10 mg |
| Sodium carboxymethylstarch | 22 mg |

-continued

| | |
|---|---|
| Talc | 10 mg |
| Magnesium stearate | 2 mg |
| Colloidal silica | 2 mg |
| Hydroxymethylcellulose, glycerol, titanium oxide (72/3.5/24.5) mixture qs for 1 finished film-coated tablet containing | 245 mg |

Example 4C

An injectable solution containing 50 mg of active product having the following composition is prepared:

| | |
|---|---|
| Active product | 50 mg |
| Benzoic acid | 80 mg |
| Benzyl alcohol | 0.06 ml |
| Sodium benzoate | 80 mg |
| Ethanol at 95% | 0.4 ml |
| Sodium hydroxide | 24 mg |
| Propylene glycol | 1.6 ml |
| Water qs for | 4 ml |

What is claimed:

1. A compound of general formula

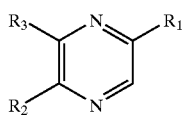
(I)

in which:

$R_1$ represents a stereoisomeric form of the chain

—(CHOH)$_3$—CH$_2$—O—COR (II), $R_2$ represents a hydrogen atom and $R_3$ represents a stereoisomeric form of the chain

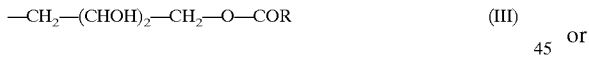
—CH$_2$—(CHOH)$_2$—CH$_2$—O—COR (III)

or $R_2$ represents a stereoisomeric form of the chain

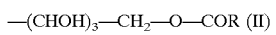
—(CHOH)$_3$—CH$_2$—O—COR (II)

or

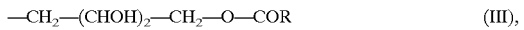
—CH$_2$—(CHOH)$_2$—CH$_2$—O—COR (III), $R_3$ represents a hydrogen atom, R represents an -(Alk)i-(Cycloalk) radical, for which:

Alk denotes an alkyl radical that means a saturated straight- or branched-chain hydrocarbonaceous radical comprising 1 to 6 carbon atoms, Cycloalk denotes a cycloalkyl radical that means a saturated cyclic hydrocarbonaceous radical comprising 5 or 6 carbon atoms, and i is equal to 0 or 1;

or a stereoisomeric form thereof or pharmaceutically acceptable salt thereof with an inorganic or organic acid.

2. The compound according to claim 1 of general formula (IV), (V) or (VI):

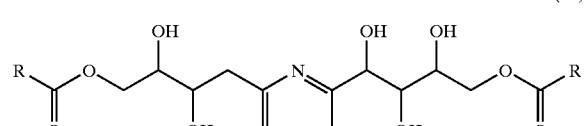
(IV)

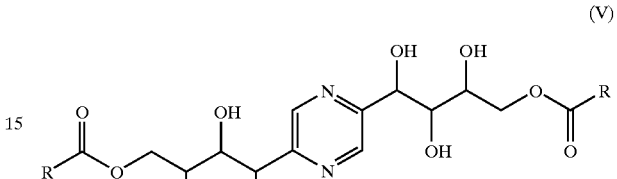
(V)

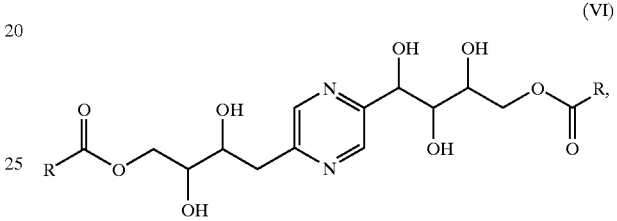
(VI)

in which

R represents an -(Alk)i-(Cycloalk) radical, for which:

Alk denotes an alkyl radical that means a saturated straight- or branched-chain hydrocarbonaceous radical comprising 1 to 6 carbon atoms, Cycloalk denotes a cycloalkyl radical that means a saturated cyclic hydrocarbonaceous radical comprising 5 or 6 carbon atoms, and i is equal to 0 or 1;

or a stereoisomeric form thereof or pharmaceutically acceptable salt thereof with an inorganic or organic acid.

3. A compound according to claim 1 of general formula (VII), (VIII) or (IX):

(VII)

(VIII)

-continued (IX)

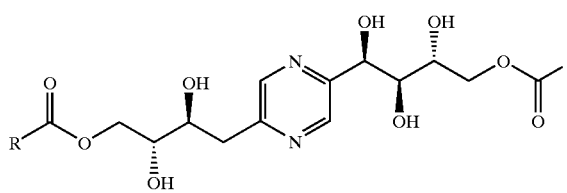

in which

R represents an -(Alk)i-(Cycloalk) radical,
for which:
Alk denotes au alkyl radical that means a saturated straight- or branched-chain hydrocarbonaceous radical comprising 1 to 6 carbon atoms,
Cycloalk denotes a cycloalkyl radical that means a saturated cyclic hydrocarbonaceous radical comprising 5 or 6 carbon atoms, and i is equal to 0 or 1;
or
a pharmaceutically acceptable salt thereof with an inorganic or organic acid.

4. The compound to claim 1 of general formula (IX):

(IX)

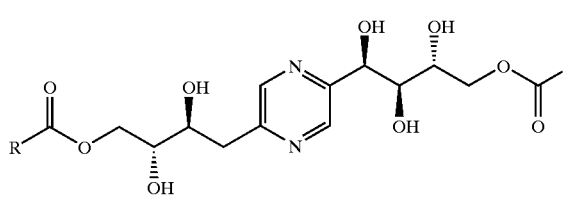

in which:

R represents an -(Alk)i-(Cycloalk) radical,
for which:
Alk denotes an alkyl radical that means a saturated straight- or branched-chain hydrocarbonaceous radical comprising 1 to 6 carbon atoms,
Cycloalk denotes a cycloalkyl radical that means a saturated cyclic hydrocarbonaceous radical comprising 5 or 6 carbon atoms, and
i is equal t 0 or 1;
or
a pharmaceutically acceptable salt thereof with an inorganic or organic acid.

5. The compound according to claim 1 for which:
R represents an -(Alk)i-(Cycloalk) radical,
for which:
Alk denotes the methyl radical,
Cycloalk denotes a cyclohexyl radical, and
i is equal to 0 or 1;
or
a stereoisomeric form thereof or pharmaceutically acceptable salt thereof with an inorganic or organic acid.

6. The compound according to claim 2 for which:
R represents an -(Alk)i-(Cycloalk) radical,
for which:
Alk denotes the methyl radical,
Cycloalk denotes a cyclohexyl radical, and
is equal to 0 or 1;
or a stereoisomeric from thereof or pharmaceutically acceptable salt thereof with an inorganic or organic acid.

7. The compound according to claim 3 for which:
R represents an (Alk)i-(Cycloalk) radical,
for which:
Alk denotes the methyl radical,
Cycloalk denotes a cyclohexyl radical, and
i is equal to 0 or 1;
or
a pharmaceutically acceptable salt thereof with an inorganic or organic acid.

8. The compound according to claim 4 for which:
R represents an -(Alk)i-(Cycloalk) radical,
for which:
Alk denotes the methyl radicals
Cycloalk denotes a cyclohexyl radical, and
i is equal to 0 or 1;
or
a pharmaceutically acceptable salt thereof with an inorganic or organic acid.

9. The compound according to claim 1 which is
4,4''-O,O-dicyclohexyloyl-2-[(1R,2S,3R)(1,2,3,4-tetrahydroxybutyl)]-5-[(2'S, 3'R)(2',3',4'-trihydroxybutyl)]pyrazine, or
4,4'-O,O-dicyclohexyloyl-2-[(1R,2S,3R)(1,2,3,4-tetrahydroxybutyl)]-5-[(2'S,3'R)-(2',3',4'-trihydroxybutyl)]pyrazine,
or
a pharmaceutically acceptable salt thereof with an inorganic or organic acid.

10. The compound according to claim 1 which is 4,4'-O,O-Dicyclohexyloyl-2-[(1R,2S,3R)(1,2,3,4-tetrahydroxybutyl)]5-[(2'S,3'R)(2',3',4'-trihydoxybutyl)]pyrazine,
or
a pharmaceutically acceptable salt thereof with an inorganic or organic acid.

11. A process for the preparation of the compound according to claim 1, comprising reacting a compound of general formula:

(X)

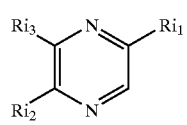

in which:

Ri1 represents a stereoisomeric form of the chain $$—(CHOH)_3—CH2OH \qquad (XI),$$

Ri2 represents a hydrogen atom and Ri3 represents a stereoisomeric form of the chain $$—CH_2—(CHOH)_2—CH2OH \qquad (XII)$$

or

Ri2 represents a stereoisomeric form of the chain $$—(CHOH)_2—CH2OH \qquad (XI)$$

or

 (XII)

and Ri3 represents a hydrogen atom,
with an acyl halide of formula R-COX, in which R is defined as in claim 1 and X represents a halogen atom.

12. The process according to claim 11, wherein the reaction is carried out in the presence of pyridine between 0 and 40° C.

13. A pharmaceutical composition comprising a pharmaceutically appropriate dosage of a compound according to claim 1 and a pharmaceutically compatible excipient.

14. A method of treating glycemia in a human comprising administering to the human pharmaceutically appropriate dosage of the compound of claim 1.

* * * * *